(12) United States Patent
Petrini et al.

(10) Patent No.: US 9,066,934 B2
(45) Date of Patent: *Jun. 30, 2015

(54) COMPOSITE MATERIAL COMPRISING PECTIN AND CALCIUM PHOSPHATE AND METHOD FOR ITS REALISATION

(75) Inventors: Paola Petrini, Milan (IT); Maria Cristina Tanzi, Milan (IT); Liliana Giuliano, Casteltermini (IT); Fabiola Munarin, Giussano (IT); Pierfrancesco Robotti, Nago-Torbole (IT); Giacomo Bianchi, Borgo Valsugana (IT)

(73) Assignee: EUROCOATING S.P.A., Pergine Valsugana (Trento) (IT)

( * ) Notice: Subject to any disclaimer, the term of this patent is extended or adjusted under 35 U.S.C. 154(b) by 0 days.

This patent is subject to a terminal disclaimer.

(21) Appl. No.: 13/809,855

(22) PCT Filed: Jul. 13, 2011

(86) PCT No.: PCT/IB2011/053136
§ 371 (c)(1),
(2), (4) Date: Mar. 28, 2013

(87) PCT Pub. No.: WO2012/007917
PCT Pub. Date: Jan. 19, 2012

(65) Prior Publication Data
US 2013/0177656 A1    Jul. 11, 2013

(30) Foreign Application Priority Data
Jul. 13, 2010  (IT) ................ VR2010A0140

(51) Int. Cl.
*A61K 33/42* (2006.01)
*A61L 27/42* (2006.01)

(52) U.S. Cl.
CPC ............... *A61K 33/42* (2013.01); *A61L 27/425* (2013.01)

(58) Field of Classification Search
None
See application file for complete search history.

(56) References Cited

U.S. PATENT DOCUMENTS

| | | | | |
|---|---|---|---|---|
| 4,136,209 | A | * | 1/1979 | Fox ................... 426/577 |
| 5,980,625 | A | | 11/1999 | Sawamura et al. |
| 7,494,669 | B2 | * | 2/2009 | Ni et al. ............ 424/488 |
| 8,083,851 | B2 | * | 12/2011 | Crudden et al. ...... 106/724 |

FOREIGN PATENT DOCUMENTS

DE    4103876   *  8/1991

OTHER PUBLICATIONS

S. Girod Fullana, et al., Controlled Release Properties and Final Macroporosity of a Pectin Microspheres-Calcium Phosphate Composite Bone Cement, Acta Biomaterialia 6 (2010) 2294-2300.

* cited by examiner

*Primary Examiner* — Robert A Wax
*Assistant Examiner* — Danah Al-Awadi
(74) *Attorney, Agent, or Firm* — Tutunjian & Bitetto, P. C.

(57) ABSTRACT

A method for obtaining a composite material including an aqueous solution of pectin and a suspension/solution of calcium phosphate mixed together, wherein said solution of pectin cross-links with a portion of the calcium obtained from the solution of calcium phosphate and wherein a portion of the calcium phosphate in suspension remains as inorganic phase and composite materials obtained by this method.

16 Claims, 5 Drawing Sheets

COMPOSITE MATERIAL COMPRISING PECTIN AND CALCIUM PHOSPHATE AND METHOD FOR ITS REALISATION

TECHNICAL FIELD OF THE INVENTION

The present invention relates to a method for the realisation of a composite material comprising pectins and calcium phosphate, wherein the pectins are cross-linked by calcium phosphate; the composite material obtained by such method and the use of such composite material.

DESCRIPTION OF RELATED ART

Pectins are hetero-polysaccharides isolated from the cell wall of plants and are widely used in the food and pharmaceutical industries. Peptide polysaccharides have a very complex structure and belong to the family of polyuronic acids, such as alginate and hyaluronic acid, characterized by the presence of carboxylic groups which, depending on the pH, can be deprotonated making the polysaccharide negative. The amount of carboxylic groups can vary, changing the characteristics of pectins. In particular, pectins contain 1,4-α-D galacturonic acid, with a variable number of carboxyl groups present in the form of methyl-ester groups. There are also some branches which contain neutral monosaccharide units (galactose and rhamnose).

Recent studies are showing that the branching, in general, imparts special properties to such peptide polysaccharides against several cell types and in particular, they may contribute to a better cell adhesion.

The degree of esterification (DE) is used to rank pectins into high methoxyl (HM, DE>50) or low methoxyl (LM, DE<50) pectins.

Pectins may be dissolved in water, but once cross-linked, they form water insoluble gels, with properties that depend on the type and degree of cross-linking, also depending on the degree of esterification.

HM pectins require very low pH for gel formation, whereas LM pectins form gels by cross-linking in the presence of divalent and trivalent cations.

The cross-linking agents typically used are the calcium and iron chlorides, commonly used in the formation of micro- and nano-particles or coatings. The kinetics of gelification determined by such compounds, however, is very fast and therefore it is difficult to control. Similarly to what happens with alginates, this represents a significant drawback for the preparation of injectable and/or bulk gels, where homogeneity is an essential requisite.

In general, organic calcium salts are better tolerated from a physiological point of view: for example, it is possible to obtain gel from calcium gluconate, although in this case, the gelification kinetics is fast compared to what happens with the calcium phosphate, as explained hereinafter.

In order to obtain a more homogeneous gelification using the above cross-linking agents, complex methodologies have been developed, such as cross-linking induced by diffusion. The results of this method, however, are not satisfactory in terms of homogeneity of the resulting product.

Alternatively, calcium is released from little soluble calcium salts such as calcium carbonate, calcium citrate and calcium EDTA. The release of calcium is achieved through the progressive lowering of the pH of the solution induced by the degradation of a molecule that is slowly hydrolyzed, such as δ-gluconolactone. These gels, however, are prepared in conditions of lack of calcium and their mechanical properties are poor compared to those of gels obtained from solutions of calcium chloride.

The viscosity of a gel increases as a result of cross-linking, and depends on the amount of cross-linker and the degree of esterification of pectin. The properties range from a viscous gel to solid materials. The properties are highly dependent on the molecular weight of pectin and on the pH of the environment.

Various pectins with different molecular weight and different degree of esterification are available on the market.

The technology in the biomedical field for the creation of biocompatible materials for use in various industries (cosmetic surgery, implantology, treatment of injuries, etc.), is having a remarkable development.

The research is aimed mainly at identifying new substances and/or materials that improve the features of compatibility with the surrounding tissues, have good mechanical properties and a speed of resorption adjustable according to the application. The materials usually applied in the medical field can be assigned to various areas.

Within the scope of cosmetic surgery, for example, injectable gels usually used, based on hyaluronic acid and collagen, are used for various applications such as: lip augmentation, correction of superficial scars, fine lines and wrinkles, naso-labial folds, increases in volume, etc. In general, injectable gels are divided into materials with rapid resorption kinetics (3-6 months), medium term (6-12 months) and permanent injectable gels.

The materials based on hyaluronic acid may contain, as a radical scavenger, mannitol, in order, as a result of material implant, to limit the damage of the inflammatory response and increase the residence time of the same material.

These materials, however, exhibit the following drawbacks: biological risk, especially when there are human or animal derivatives, risk of allergies, poor stability and high costs.

Within the scope of bone substitutes, the materials most used for such application are autologous bone (autograft), homologous bone (allograft), heterologous material such as DBM (Demineralized Bone Matrix) and collagen, synthetic materials such as tricalcium phosphates and hydroxyapatite. These materials generally have good biological properties, such as osteogenesis but also exhibit some drawbacks. For example, the use of autologous bone has a limited availability and very high morbidity, associated with the double operation, and phenomena of pain persistence for the patient. As regards the use of homologous bone, the risks are mainly related to the risk of transmission of infectious diseases and the techniques used to reduce this risk affect the biological properties of implants, reducing the intrinsic osteogenetic and osteoconductive potential. The heterologous material does not allow a structural support, while synthetic materials have poor osteogenic properties and variable mechanical properties depending on the type of material used. 95% of these calcium phosphates are resorbed in 26 to 86 weeks.

Within the scope of the treatment of cartilage defects, the materials used in commercial products available to date are esterified hyaluronic acid and collagen, which have a proven clinical experience and good tolerability. In terms of research, materials have been used such as polyurethanes, polycarbonates, polylactic acid and polyglycolic collagen, fibrin, chitosan optionally combined with polygalacturonic acid, silk, alginates and agarose. In particular, using chitosan it is not possible to incorporate cells within the gel matrix that is formed.

However, none of the techniques commonly used in the prior art has given incontrovertible results to date and is free from side effects.

As regards, on the other hand, the treatment of skin lesions, arising from various factors, occlusive bandages, hydrocolloids and hydrogels are currently being used, resulting in healing in moist conditions. However, despite the high availability of bandages currently on the market, there are no comparative trials to date sufficient to establish a marked benefit of a particular product. For chronic lesions, moreover, no products designed specifically for their care are available.

U.S. Pat. No. 5,980,625 describes the use of a cement formed by mixing a solution of pectins with a calcium phosphate powder. The cement described by such patent differs from a gel material, wherein a solution of pectin is cross-linked with a solution of calcium phosphate. The mechanical properties of bone cement, in fact, are very different from those of a gel and the water content is different. Moreover, in such patent the ratio between pectin percentages and calcium phosphate powder percentages is to the advantage of the latter.

The document "Controlled release properties and final macroporosity of a pectin microspheres-calcium phosphate composite bone cement," Girod Fullana, et al., Acta Biomaterialia, vol. 6 (6), pages 2294-2300, describes a bone cement wherein starched pectin microspheres preformed with calcium chloride are loaded into a mass of bone cement based on calcium phosphate. In this document, the pectin microspheres serve substantially as a porogenic agent without leading to an actual link between the pectin and calcium phosphates. Also in this case, the cement described by such document differs from a gel material, wherein a solution of pectin is cross-linked with a solution of calcium phosphate. The mechanical properties of bone cement, in fact, are very different from those of a gel.

Materials consisting of pectins are known, both of the high-methoxyl (HM) and low methoxyl (LM) type, and calcium phosphate blended together. In these materials, pectin serves as porogenic or plasticizing agent for forming materials in the form of a paste. Usually, no linking reactions occur in these materials between pectin and calcium phosphate and the ratio between such components is to the benefit of calcium phosphate.

There is therefore a need to identify a composite material with gel features, obtained by the reaction and cross-linking of a solution of pectins with a solution containing material analogous to human bone components, such as calcium phosphate, and with slow and therefore highly controllable cross-linking kinetics.

SUMMARY OF THE INVENTION

An object of the invention is to improve the prior art.

Another object of the invention is to provide a method that is simple and easy to implement.

A further advantage of the invention is to provide a method wherein there are only two main components.

Another object of the present invention is to provide a method which is inexpensive compared to known methods.

According to one aspect of the present invention, these objects are achieved by a method for making a composite material as specified in the present disclosure.

A further object of the present invention is to provide a material with improved mechanical and biocompatibility properties.

A further object of the present invention is to provide a composite material that may be obtained quickly and inexpensively.

According to one aspect of the present invention, a composite material is provided as specified in the present disclosure.

BRIEF DESCRIPTION OF THE DRAWINGS

Further features and advantages of the invention will become more apparent from the detailed description of a method for making a composite material and composite materials obtained with such process, illustrated by way of a non-limiting example, in the attached drawings, wherein.

DETAILED DESCRIPTION OF EMBODIMENTS OF THE INVENTION

The method object of the present invention comprises the following various steps.

A first step of the method object of the present invention consists in preparing a solution/suspension of calcium phosphate at a concentration of 0.1-10% weight/volume. The percentage used preferably varies between 0.25% and 5% weight/volume and more preferably between 0.25% and 3% weight/volume.

The above concentrations, as in the remaining part of this specification, report the commonly used words "weight/volume" which indicate the amount of solute, i.e. its mass, for a given volume of solution. The "weight/volume" is therefore to be considered equivalent to "mass/volume" since the measurements should be made in an environment in which the force of gravity, which determines the weight of a substance, may be considered constant at any point and therefore negligible.

The calcium phosphates used consist of hydroxyapatite and/or are in other forms, non-crystalline or crystalline. The following types of calcium phosphate may also be present, alone or in combination: calcium phosphate $Ca_3(PO_4)_2$, calcium dihydrogen phosphate $Ca(H_2PO_4)_2$, calcium hydrogen phosphate $CaHPO_4$, tricalcium phosphate, β or α $Ca_3(PO_4)_2$, tetracalcium phosphate $Ca_4(PO_4)_2$, hydroxyapatite $Ca_{10}(PO_4)_6(OH)_2$.

Other possible types of calcium phosphate are: acid calcium phosphate, calcium dihydrogen phosphate, calcium glycerophosphate, calcium hydrogen phosphate, calcium lactophosphate, tribasic calcium phosphate, calcium-o-phosphate, calcium pyrophosphate, calcium succinate, calcium tetraphosphate and calcium phosphate compositions obtained with other substances.

The mixing of the solution/suspension of calcium phosphates occurs for a time between 1 second and 30 minutes at room temperature. The resulting solution has a neutral or slightly alkaline pH.

The temperature can vary from room temperature and this changes the features of the suspension. The temperature, in fact, varies the solubility of calcium phosphates, as well as pH and mixing time, and therefore the quantity of calcium ions in solution, which is linked to the degree of pectin cross-linking that may be obtained. In addition, calcium ions released from the calcium phosphates listed above allow obtaining a composite material that may not be obtained with calcium-based substances commonly used in the prior art, such as calcium chloride.

More generally, the temperature can range from 0° C. to 100° C. and the mixing time can vary from 1 second to 25 hours. The pH of the suspension/solution of calcium phosphates may be changed from neutral pH to acidic pH.

The mixing time, pH and temperature vary the percentage of calcium phosphates dissolved in the solution.

A second step of the method object of the present invention consists in preparing an aqueous solution of pectin present at concentrations of 0.2-10% weight/volume.

The pectins preferably used are pectins extracted from the lemon peel and/or of different origin with a degree of esterification of between 5% and 50%, in particular pectins with a degree of esterification of 40% and/or 42%.

In one embodiment of the invention, the molecular weight of these substances usually varies between 40 and 350 KDa.

In a further embodiment of the invention, the molecular weight of pectins varies between 15 and 1000 KDa.

These pectins are dissolved in the aqueous solution at the percentage listed above at room temperature for 12 hours; the solution obtained has an acidic pH. These pectins can also be dissolved at a higher temperature: the temperature increase reduces the time of dissolution of the pectins.

This aqueous solution of pectins may be obtained in an alternative embodiment, at a temperature of about 80° C. for 2 hours. In a further embodiment, such solution may be obtained at 40° C. for 2 hours. More generally, the temperature may be between 0° C. and 100° C. and the mixing time may vary from 1 second to 25 hours.

The pH of the solution may be made neutral by the addition of bases.

The preparation of the pectin solution above can also be achieved with known methods generally used for pectins or other similar polysaccharides.

The method of the present invention can be extended to all anionic polysaccharides, similar to pectin, and all changes that may be made fall within the scope of protection of the present invention.

A subsequent step of the method object of the present invention consists in mixing the solution of pectin and the suspension/solution of calcium phosphates.

This mixing process can take place instantaneously by mixing equal quantities by volume of the two solutions above at room temperature for a time ranging between 5 and 10 seconds at an acidic or neutral pH.

Such mixing may take place in an alternative embodiment, by gradually adding 1 part of suspension/solution of calcium phosphates to 0.2-2 parts of pectin solution, or preferably, to 0.4-2 parts of pectin solution. The temperature used in this case can be between 4° C. and 80° C. for a period of up to 30 minutes and obtaining a solution with neutral or slightly alkaline pH.

This method has the advantage of being able to dose the amounts and vary them in order to obtain composite materials with different features applicable to different sectors and with improved stability properties.

This method has the following advantages: the use of a component, such as calcium phosphates, naturally present in the human body and therefore highly biocompatible and the cross-linking reaction of pectins with calcium phosphate is slow and can therefore be controlled. Thus, the composite material in the form of gel obtained from such cross-linking is homogeneous, and the cross-linking effect can be evaluated in advance. In addition, the percentages of pectin and calcium phosphate are substantially equivalent or are in favor of a greater amount of pectin. The structure of the composite material obtained has a high water content and mechanical and shape properties specific of substances in the form of a gel.

Once the mixing has been obtained, the solution/suspension of pectin and calcium phosphates can be poured into a syringe or into a mold and let to gel for about 24 hours. The gelification time may vary depending on the desired application. During this period of gelification, wherein a composite material is formed, the cross-linking of pectins takes place with at least one portion of the calcium phosphate present in solution for forming a polymeric compound with a gelatinous consistency. At least a second part of the remaining calcium phosphate, not present in solution, remains, as inorganic part, trapped inside such polymeric compound formed as a result of the cross-linking, and is a filler which gives better mechanical and reinforcing properties compared to the cross-linked polymers of the prior art, which have no filler.

The method according to the invention has the advantage, compared to the prior art, to obtain the cross-linking reaction of pectins starting from calcium phosphate, rather than calcium chloride that is typically used, and hence to combine in a single process step both the cross-linking of pectins and the incorporation of the inorganic part into the same. Furthermore, in such method, the main structural components are pectins and calcium phosphate, while there may be additives or other molecules or substances which, if present, impart secondary properties to the composite material obtained by such method.

Thus, the advantage of speeding up the production method, basically consisting of a single step, adds up to the advantage of having few essential components, making the production itself more economical.

In particular, a step of such method may provide for the addition of mannitol to a final concentration of mannitol between 50-500 mM. In particular, the final concentration of mannitol is 220 mM.

The addition of mannitol takes place dissolving the same in the solution of pectin, which is then mixed, as described above, to the solution/suspension of calcium phosphates.

This substance, which is a chiral alditol, with six hydroxyl groups in the aliphatic chain consisting of six saturated carbon atoms, is a substance that can be easily found naturally in algae and fungi, and the name is derived from the manna, the sap of ash, from which it may be obtained.

The addition of mannitol allows increasing the stability to ionizing radiations and thermal stresses, thus preventing degradation effects related to the sterilization steps and to the duration (shelf life) of the material itself.

The permanence of an inorganic calcium phosphate phase in the suspension/solution is caused by the relative concentration of calcium phosphates and pectins, but also by the values of pH, temperature, time of stirring of the suspension/solution of calcium phosphates, and type and crystallinity of the calcium phosphate used. In other words, the inorganic fraction of calcium phosphate that is not dissolved depends on the features of the method according to the invention, which have effect on the same solubility of calcium phosphates.

In addition to the mechanical properties, the calcium phosphate particles, constituting the filler, improve the biological and biocompatibility features of the composite material object of the present invention, e.g. stimulating the production of collagen or other useful substances at the site where such material is introduced. The method according to the present invention may comprise the steps of loading the composite material with substances that are active towards the reduction of the infection, such as metal ions and/or topical antimicrobial drugs and/or pre-loading the calcium phosphate with metal ions known for their antibacterial effectiveness, such as, for example, silver and zinc and/or conveying, through the pectin, drugs and/or specific medicinal substances.

The present invention also includes a composite material comprising pectin and calcium phosphate blended together, wherein the calcium phosphate has a concentration of between 0.1 and 10% weight/volume, and comprising pectin cross-linked with at least one portion of the calcium phosphate and at least one second portion of the calcium phosphate trapped to form an inorganic phase of calcium phosphate.

Pectin is present in aqueous solution at a concentration between 0.2 and 10% weight/volume.

Pectin has a percentage of esterification of between 5% and 50% or 42% or 40%.

The pectins according to the present invention have a molecular weight between 40 and 350 kDa, or between 15 and 1000 kDa.

Calcium phosphate is present in aqueous solution/suspension at a concentration of between 0.25% and 5% weight/volume or between 0.25% and 3%.

Such calcium phosphate comprises one or more of the following types: calcium phosphate $Ca_3(PO_4)_2$, calcium dihydrogen phosphate $Ca(H_2PO_4)_2$, calcium hydrogen phosphate $CaHPO_4$, tricalcium phosphate β or α $Ca_3(PO_4)_2$, tetracalcium phosphate $Ca_4(PO_4)_2$, hydroxyapatite $Ca_{10}(PO_4)_6(OH)_2$, acid calcium phosphate, calcium glycerophosphate, calcium lactophosphate, calcium carbonate and magnesium, tribasic calcium phosphate, calcium-o-phosphate, calcium pyrophosphate, calcium succinate, calcium and phosphate compositions obtained with other substances.

The composite material according to the present invention is a hydrogel. It includes equal parts of the pectin solution and the solution/suspension of calcium phosphate mixed together or it comprises from 0.2 to 2 parts of the solution of pectin, or preferably 0.4 to 2 parts of the solution of pectin, and a part of the solution/suspension of calcium phosphate.

The composite material according to the present invention further includes mannitol. Mannitol has a final concentration of between 50 and 500 mM or 220 mM. The composite material according to the present invention is obtained for use in medical applications as a medicine for aesthetic applications and/or the treatment of skin lesions and/or for the treatment of cartilage defects and/or the bone substitution and/or for similar applications.

The composite material according to the present invention can be loaded with active substances in relation to the reduction of the infection, such as metal ions and/or topical antimicrobial drugs and/or calcium phosphate may be pre-loaded with metal ions known for their antibacterial effectiveness such as, for example, silver and zinc and/or the pectin may be suitable for conveying drugs and/or specific medicinal substances.

Figure 1:
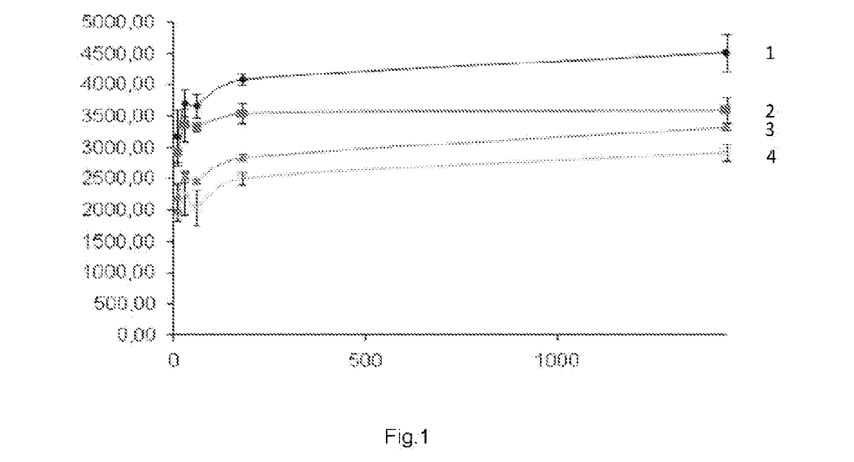
FIG. 1 is a graph of the percentage swelling rate at 24 hours in water at 37° C. of a composite material composed of 2% pectin and percentages of 0.5% (line with diamonds, 1), 1% (line with squares, 2), 2% (line with triangles, 3) and 3% (line with crosses, 4) of calcium phosphates obtained by the method object of the present invention.
Figure 2:
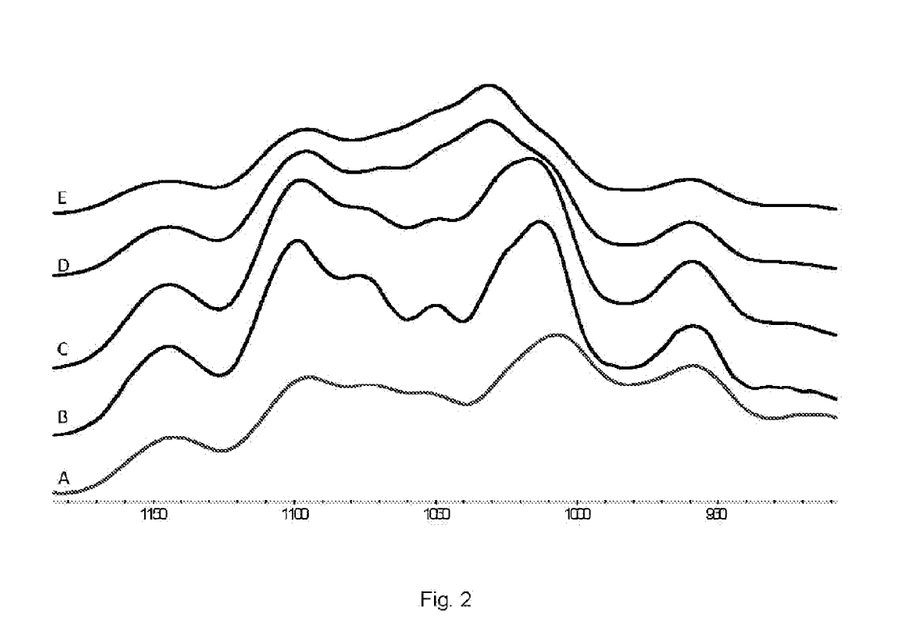
FIG. 2 is a graph comparing the FT-IR spectra for dried pectin and calcium chloride gels (line A), a solution of pectin and calcium phosphates at 0.5% (line B), 1% (line C), 2% (line D), 3% (line E) obtained as indicated in example 1; the X axis indicates the wavelength in $cm^{-1}$.
Figure 3:
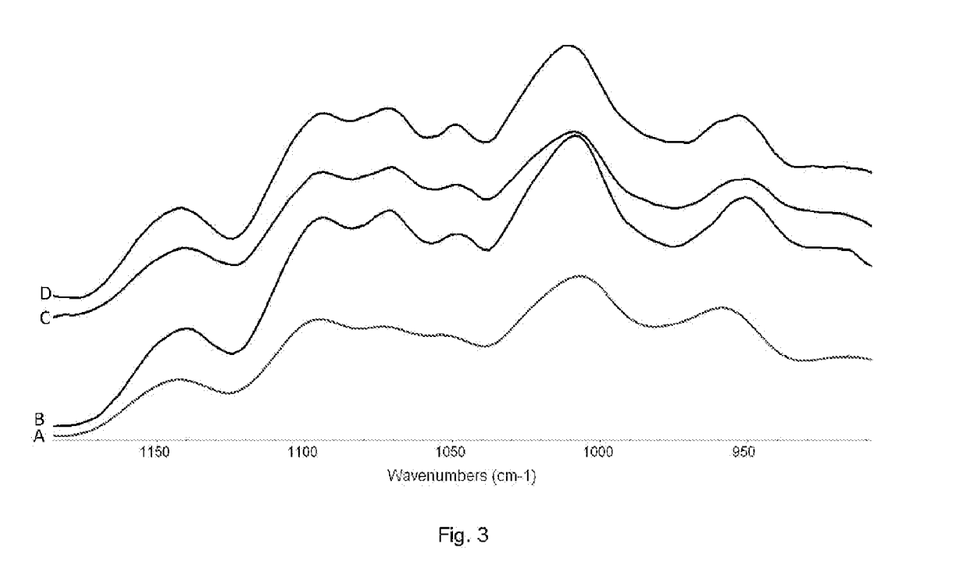
FIG. 3 is a graph comparing the FT-IR spectra for dried pectin and calcium chloride gels (line A), a solution of 2% pectin and calcium phosphate at 0.25% (line B), pectin at 3% and calcium phosphate at 0.25% (line C), pectin at 4% and calcium phosphate at 0.25% (line D); the X axis indicates the wavelength in $cm^{-1}$.

Examples 1-6 below, and the respective tables 1-9, show some embodiments of the method according to the invention for obtaining a composite material with specific features. Based on the materials obtained according to examples 1 and 2, stability tests, analysis to evaluate the total content of water, tests of swelling in water, as shown in FIG. 1, infrared spectroscopy, as shown in FIGS. 2 and 3, analysis of injectability and extrudability of the composite material, etc., have subsequently been performed. This composite material may be used with various applications in the medical field. In fact, such composite material, present in the form of injectable gel, may be used for aesthetic applications, such as: lip augmentation, correction of superficial scars, fine lines and wrinkles, naso-labial folds, increases in volume, etc.

The advantages of the use of such composite material for this application are as follows: biological advantages, such as the absence of human-derivatives and therefore safe use, reduced risk of allergies, optimal distribution in the implant site, excellent fluidity, minimization of application pain, bioactivity (stimulation of collagen production), excellent biodegradability, associated with a persistence of the volumizing effect for the required time (usually 3-6 months), degradation modulated according to the expected time of implant and higher stability, commercial advantages, such as the use of material of natural origin, productivity advantages, such as the use of a composite material prepared by a simple and fast method consisting of a single production step.

An example of material used for such applications can be represented by table 3 and/or may occur according to other parameters described in the examples herein.

Additionally, such composite material may also be applied in the treatment of skin lesions. A composite material according to the invention, modulated in order to obtain a membrane or a three-dimensional support should possess, in addition to the advantages already mentioned for the previous applications (biological, commercial and production advantages), an advantage related to the possibility of loading such material with active substances in relation to the reduction of the infection, such as metal ions, or topical antimicrobial drugs. Further possibilities presented by such composite material are: pre-loading the calcium phosphate contained therein with metal ions known for their antibacterial effectiveness, such as, for example, silver and zinc; using the solution of pectin as a carrier for specific drugs.

It is also possible with the innovative process object of the patent, to produce microspheres suitable for drug delivery that could be incorporated in the bandage material used in the treatment of such skin lesions.

The composite material used for this purpose has the following features: high biocompatibility, absence of induced allergic phenomena, maintaining high humidity at the interface, capability of absorbing excess exudate and providing proper thermal insulation, possibility of removal without trauma, high mechanical resistance also at the hydrated state, selective permeability to gases but not to pathogens.

An example of material used for such applications can be represented by table 4 and/or may occur according to other parameters described in the examples herein.

The composite material may also be used for the treatment of cartilage defects, such as a three-dimensional support, presenting the following advantages: biological advantages (no human-derivatives, low or no risk of allergies, degradability modulated depending on the application, higher stability compared to hyaluronic acid) and productivity advantages (composite material prepared by a single production step). The use of a composite material can also result in improved mechanical performance compared to single-component materials.

The composite material used for this purpose has the following features: biocompatibility, excellent cellular adhesion and three-dimensional structure suitable for cellular proliferation, high porosity, gradual bio-resorption without the release of acids and with stimulation of the formation of natural cartilage tissue, high mechanical properties.

An example of material used for such applications can be represented by table 6 and/or 8 and/or may occur according to other parameters in the examples described herein.

This composite material, however, may also be used as an injectable gel. Such injectable gel may be loaded with cellular components that are embedded within the matrix itself, to allow a therapy usable by minimally invasive surgery in a single step. The injectable gel may also be formulated to allow a cross-linking in situ, allowing the entrapment of the preloaded cellular components and creating an environment suitable for the maintenance of cellular viability and formation of extracellular matrix, optimal conditions for the care of these cartilage defects.

An example of material used for such applications can be represented by table 5 and/or may occur according to other parameters described in the examples herein.

With this composite material is also possible to obtain bone substitutes to use in dentistry to cure periodontal defects, extra-alveolar defects, bone lesions, cystic cavities, intrabony defects, the maxillary sinus lift, the increase of the alveolar bridge, endodontic perforations, post-extraction sites, etc.; in orthopedics for treating fractures of the tibial head, distal radius, heel, proximal and distal tibia, proximal and distal femur, generic metaphysis, proximal humerus, acetabulum, tibial plateau, spine, bone cysts, autologous bone sampling sites, pseudoarthrosis, spinal fusion, generic bone defects, total hip revision, foot and hand surgery, arthroplasty, trauma, maxillofacial surgery, surgery of the skull, bone defects caused by cancer, etc.

The advantages of the composite material as a bone substitute are: as much as possible unlimited availability, rapid conversion into bone matrix, precise possibility of modulating the morphology, stability in situ, reproducible biological and mechanical features and immediate compression stability for the bone substitutes designed to withstand loads.

Another possible application of the composite material obtained by the present invention can envisage loading the same with cellular components, drugs, peptides or proteins or antibacterial agents, to form a controlled release vehicle of such active principles or of such cellular components.

Such composite material may also be used as injectable gel for applications not subject to load and be applied as a binder for using ceramic material and as filler for small bone defects such as periodontal defects.

An example of material used for such applications can be represented by table 7 and/or may occur according to other parameters described in the examples herein.

Example 1

1 ml of an aqueous solution of pectin (from lemon, H&F Italy), with a degree of esterification of 42%, contained in a mold with a diameter of 17 mm, is added, under magnetic stirring, with 1 ml of an aqueous suspension of calcium phosphates obtained by suspending the powder of calcium phosphate in ultrapure water and keeping under magnetic stirring for 30 min. The mixture of pectin/calcium phosphate is kept at room temperature for 24 hours, after this time interval, the resulting composite material in gel is extracted from the mold. The total water content of the resulting composite material in gel was found to be between 96 and 98% by weight.

Table 1 below shows the different concentrations of pectin and calcium phosphate used and the stability in water and in NaCl 0.9% w/v at least 24 hours of the resulting composite material in gel.

TABLE 1

Concentrations of pectin and calcium phosphate,
stability in water and in NaCl 0.9% w/v at 37° C.

| Pectin (% w/v) | Calcium phosphate (% w/v) | Stability in water | Stability in NaCl 0.9% w/v |
|---|---|---|---|
| 2 | 0.5 | stable | instable |
|   | 1 | stable | — |
|   | 2 | stable | — |
|   | 3 | stable | instable |
| 3 | 0.5 | stable | stable up to 60 min |
|   | 1 | — | — |
|   | 2 | — | — |
|   | 3 | stable | stable up to 30 min |
| 4 | 0.5 | stable | stable up to 180 min |
|   | 1 | — | — |
|   | 2 | — | — |
|   | 3 | stable | stable up to 180 min |

The composite gel materials at 2% pectin were lyophilized and water swelling tests were conducted thereon at 37° C., as shown in FIG. 1. The percentage of swelling in water, Water Uptake (WU %), shown in the ordinate of the diagram of FIG. 1 compared to the time in minutes indicated on the abscissa, was determined using the following formula:

$$WU\ \% = \frac{(Wr - Ws)}{Ws} \cdot 100$$

wherein: Wr is the weight of the swollen sample at a given time interval and Ws is the initial dry weight of the sample.

For the samples investigated, the percentage of swelling in water was proportional to the content of calcium phosphate and, therefore, to the degree of cross-linking of the composite material.

As shown in FIG. 2, the composite freeze-dried gels materials described above were also characterized by infrared spectroscopy (FT-IR) and compared with the spectra of a gel obtained by cross-linking pectin with $CaCl_2$.

With the increasing concentration of calcium phosphate, the progressive shift of the peak at 1008 $cm^{-1}$ of pectin to longer wavelengths is evident, due to the contribution of the peak at 1031 $cm^{-1}$ typical of calcium phosphate itself.

Example 2

1 ml of an aqueous solution of pectin (H&F Italy) is added, under magnetic stirring, with 1 ml of an aqueous suspension of calcium phosphates, obtained by suspending the powder of calcium phosphate in ultrapure water and maintaining under magnetic stirring for 10 seconds. The mixture of pectin/calcium phosphate is transferred into a 5 ml syringe.

Table 2 below shows the various concentrations of pectin and calcium phosphate used and the stability in water and in NaCl 0.9% w/v at least 24 hours of the resulting gel composite materials. The total content of water for all of such materials proved to be more than 98% by weight.

TABLE 2

Concentrations of pectin and calcium phosphate,
stability in water and in NaCl 0.9% w/v at 37° C.

| Pectin (% w/v) | Calcium phosphate (% w/v) | Stability in water | Stability in NaCl 0.9% w/v |
|---|---|---|---|
| 1 | 0.5 | — | — |
| 1.5 | 0.5 | — | — |
| 2 | 0.5 | stable up to 4 hours | instable |
|   | 0.25 | instable | instable |
| 3 | 0.25 | stable up to 4 hours | instable |
| 4 | 0.25 | stable up to 4 hours | instable |

Some of the composite gel materials listed above were dried in an stove at 37° C. to a constant weight and characterized by infrared spectroscopy, as shown in FIG. 3. Unlike what was observed for the composite gel of example 1, no contribution was observed related to the presence of calcium phosphate, due to the low concentration of the latter in the gel.

The injectability/extrudability of these composite materials was also monitored by a needle of 0.5 mm in diameter over the 24 hours after their preparation. For all samples, the viscosity increases gradually over the 24 hours, passing from the liquid state, freshly prepared, to a consistency of injectable gel.

Example 3

Figure 4:
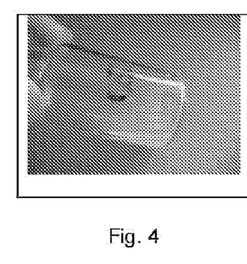
FIG. 4 shows a gel produced in accordance with the methodology and the amounts indicated in table 3 below immediately after the mixing step of the pectin solution with the calcium phosphate solution/suspension.
Figure 5:
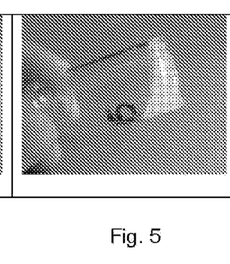
FIG. 5 shows the gel of FIG. 4 after 3 hours from mixing.
Figure 6:
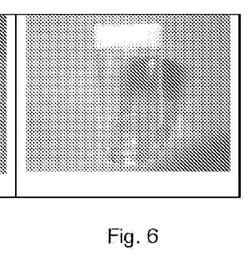
FIG. 6 a gel obtained in accordance with the methodology and the amounts indicated in table 6 below.

The tables below illustrate some embodiments of the method according to the invention for the production of composite materials comprising pectins and calcium phosphates. Depending on the method and the amounts used, gels are obtained with different properties and consistencies, as shown in FIGS. 4-6.

TABLE 3

| Method | Conditions used |
|---|---|
| Pectin | Esterification 25-49% |
|  | Molecular weight 50-120 KDa |
| Preparation of an aqueous pectin solution | 3-6% weight/volume |
|  | Bring pH a 5-6 |
| Calcium-phosphates | Crystalline (hydroxyapatite) and/or other composition |
| Preparation of a suspension/solution of calcium phosphates | 0.25-1% weight/volume |
|  | Mix 10 min |
|  | Room T |
| Mixing of the pectin solution and of the suspension/solution of calcium phosphates | Mix 1-5 minutes |
|  | Room T |

TABLE 4

| Method | Conditions used |
|---|---|
| Pectin | Esterification 35-45% |
|  | Molecular weight 120-350 KDa or up to 600 KDa |
| Preparation of an aqueous pectin solution | 3-8% weight/volume |
|  | Bring pH to 5-6 |
| Calcium-phosphates | Crystalline (hydroxyapatite) and/or other composition |
| Preparation of a suspension/solution of calcium phosphates | 0.25-1% weight/volume |
|  | Mix 1-10 min |
|  | Room T |
| Mixing of the pectin solution and of the suspension/solution of calcium phosphates | Mix instantaneously |
|  | Room T |
|  | Mixing time: 10 seconds-10 minutes |

TABLE 5

| Method | Conditions used |
| --- | --- |
| Pectin | Esterification 35-45% |
| | Molecular weight 100-150 KDa |
| Preparation of an aqueous pectin solution | 2-5% weight/volume |
| | Bring pH to 5-6 and suspend the cells in the solution (room T) |
| Calcium-phosphates | Crystalline (hydroxyapatite) and/or other composition |
| Preparation of a suspension/solution of calcium phosphates | 0.5-1% weight/volume |
| | Mix 10 sec |
| | T 4° C. |
| Mixing of the pectin solution and of the suspension/solution of calcium phosphates | Gradual addition of the calcium phosphate suspension |
| | Room T |

TABLE 6

| Method | Conditions used |
| --- | --- |
| Pectin | Esterification 10-35% |
| | Molecular weight 200-350 KDa |
| Preparation of an aqueous pectin solution | 4-5% weight/volume |
| | Bring pH to 5-6 |
| Calcium-phosphates | Crystalline (hydroxyapatite) and/or other composition |
| Preparation of a suspension/solution of calcium phosphates | 2-3% weight/volume |
| | Mix 1 hour |
| | T 80° C. |
| Mixing of the pectin solution and of the suspension/solution of calcium phosphates | Mix instantaneously |
| | Room T |
| | Mixing time: 5-10 seconds by vortex |
| | Freeze-dry |

TABLE 7

| Method | Conditions used |
| --- | --- |
| Pectin | Esterification 30-45% |
| | Molecular weight 100-350 KDa |
| Preparation of an aqueous pectin solution | 2-6% weight/volume |
| | Bring pH to 5-6 |
| Calcium-phosphates | Crystalline (hydroxyapatite) and/or from other composition |
| Preparation of a suspension/solution of calcium phosphates | 0.5-1.5% weight/volume |
| | Mix 10 sec |
| | T 4° C. |
| Mixing of the pectin solution and of the suspension/solution of calcium phosphates | Gradual addition of the calcium phosphate suspension |
| | Room T |

TABLE 8

| Method | Conditions used |
| --- | --- |
| Pectin | Esterification 10-45% |
| | Molecular weight 200-350 KDa |
| Preparation of an aqueous pectin solution | 3-10% weight/volume |
| | Bring pH to 5-6 |
| Calcium-phosphates | Crystalline (hydroxyapatite) and/or other composition |
| Preparation of a suspension/solution of calcium phosphates | 3-10% weight/volume |
| | Mix 30 minutes |
| | T 4° C. |
| Mixing of the pectin solution and of the suspension/solution of calcium phosphates | Mix instantaneously |
| | T 4-22° C. |
| | Mixing time: 5-10 seconds by vortex |

Example 4

For the preparation of injectable gels for soft tissue regeneration the gels are prepared according to table 3. In detail, a pectin with a molecular weight below 200 KDa and esterification below 35% is dissolved at room temperature to a final concentration of 6% weight/volume. The pH of the solution is brought to 5 with NaOH 0.5 M.

A part of the solution of pectin is mixed at room temperature for 10 minutes with a solution/suspension of hydroxyapatite (HA) according to an appropriate concentration and suitable ratio, as reported in table 9 below.

Figure 7:
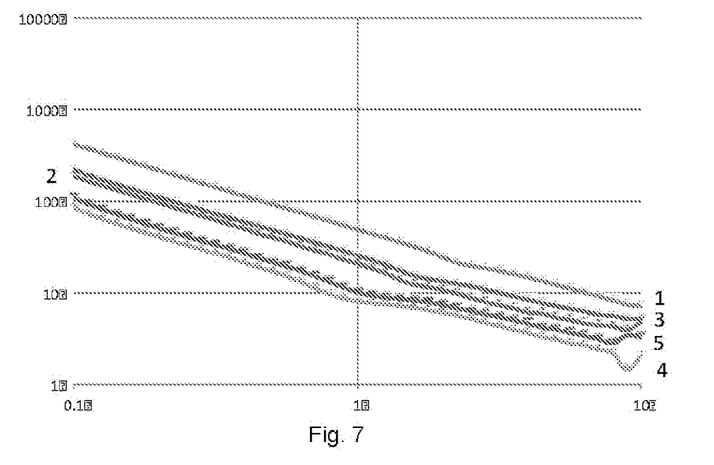
FIG. 7 shows the rheological properties of the samples mentioned in table 9 below, prepared according to example 4, where the X axis shows the frequency in Hz and the Y axis shows the complex viscosity in Pa*s. Sample 1 is shown with the clear line with x, sample 2 with the line with diamonds, sample 3 with the dark line with x, sample 4 with the line with triangles, sample 5 with the line with squares. From top to bottom, the lines of samples 1, 3, 2, 5, 4 are visible.
Figure 8:
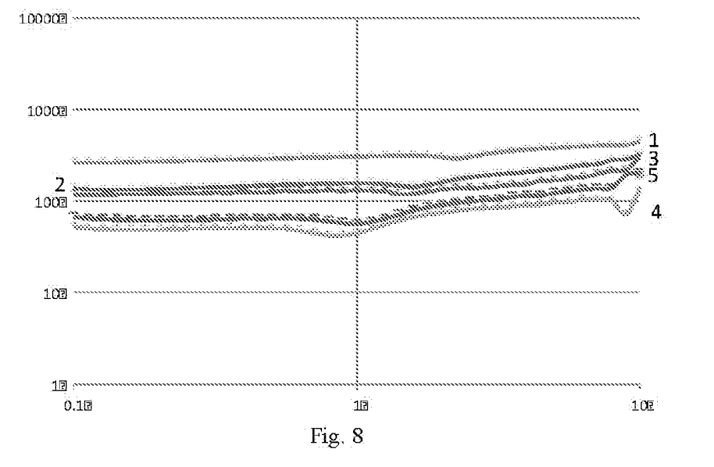
FIG. 8 shows the rheological properties of the samples indicated in table 9 below, prepared according to example 4, wherein the X axis shows the frequency in Hz and the Y axis indicates the storage module in Pa. Sample 1 is shown with the clear line with x, sample 2 with the line with diamonds, sample 3 with the dark line with x, sample 4 with the line with triangles, sample 5 with the line with squares. From top to bottom, the lines of samples 1, 3, 2, 5, 4 are visible.

The rheological properties of samples obtained were evaluated 7 days after preparation and storage at 4° C. of the same. The storage module and the complex viscosity of each gel were quantified according to oscillation measurements using a device called AX1500 Rheometer (TA), using parallel plate geometries with a distance between the plates of 1.2 mm. All oscillation measurements were made at 37° C. The oscillation measurements were taken with $\tau=5$ Pa on a frequency comprised between 0.1 Hz and 10 Hz. These measurements are shown in FIGS. 7 and 8.

Table 9 below describes the samples produced according to examples 4 and 5.

TABLE 9

| Sample | Concentration of HA (weight/volume) | Ratio between pectin solution and volume of the solution/suspension of HA |
| --- | --- | --- |
| P4H03 (1) | 0.9 | 1:0.5 |
| P3H05 (2) | 1.0 | 1:1 |
| P3H03 (3) | 0.6 | 1:1 |
| P2H05 (4) | 0.75 | 1:2 |
| P2H03 (5) | 0.45 | 1:2 |

Example 5

For the preparation of injectable gels for cartilage repair, the gel is prepared by following the method and the components listed in table 4. In detail, the pectin with molecular weight between 500 and 600 KDA and esterification of 37% was dissolved at room temperature to a final concentration of 6% weight/volume. The pH of the solution was brought to 5 with NaOH 0.5 M.

Part of the pectin solution was mixed at room temperature for 10 minutes with a solution/suspension of hydroxyapatite (HA) according to the appropriate concentration and appropriate ratios as reported in table 9.

Figure 9:
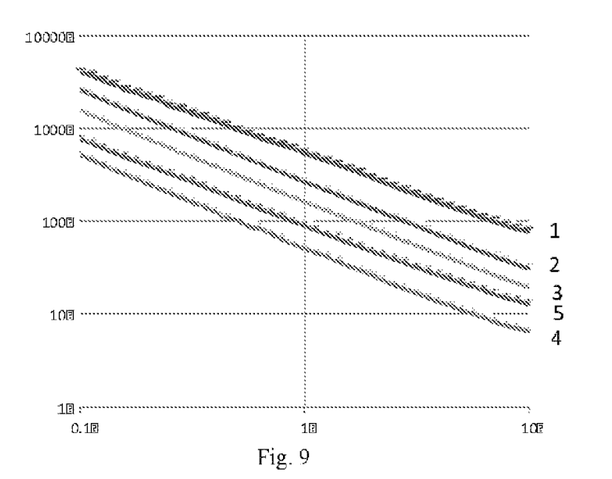
FIG. 9 shows the rheological properties of the samples mentioned in table 9 below, prepared according to example 5, where the X axis shows the frequency in Hz and the Y axis shows the complex viscosity in Pa*s. Sample 1 is shown with the line with squares, sample 2 with the dark line with x, sample 3 with the line with vertical bars, sample 4 with the clear line with x, sample 5 with the line with diamonds.
Figure 10:
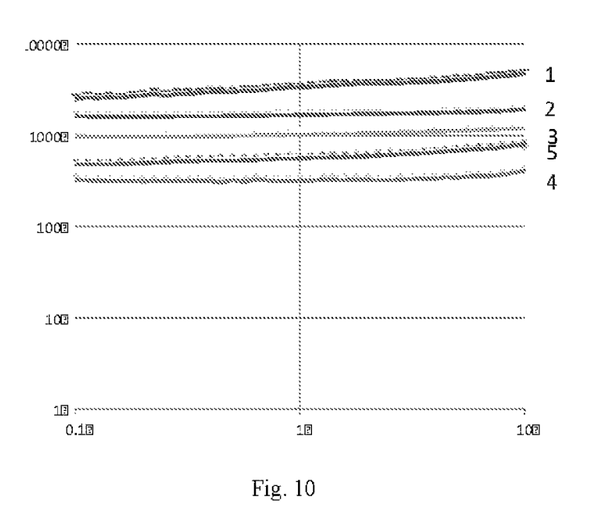
FIG. 10 shows the rheological properties of the samples indicated in table 9 below, prepared according to example 5, wherein the X axis shows the frequency in Hz and the Y axis indicates the storage module in Pa. Sample 1 is represented by the line with squares, sample 2 with the dark line with x, sample 3 with the line with vertical bars, sample 4 with the clear line with x, sample 5 with the line with diamonds.

The rheological properties of samples obtained were evaluated 7 days after preparation and storage of the same at 4° C. as described in example 4. These measures are shown in FIGS. 9 and 10.

Example 6

Figure 11:
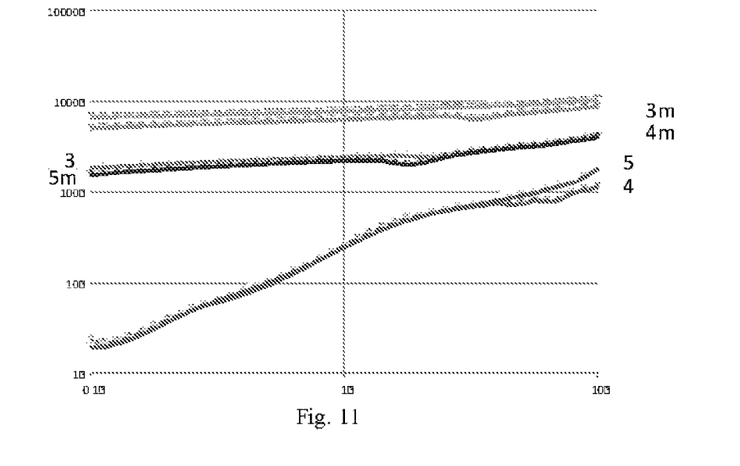
FIG. 11 shows the rheological properties of the samples indicated in table 9 below, prepared according to example 6, wherein the X axis shows the frequency in Hz and the Y axis indicates the storage module in Pa. Sample 3 is represented with the line with vertical bars, sample 3 added with mannitol (3m) with the line with squares, sample 4 with the clear line with diamonds, sample 4 added with mannitol (4m) with the clear line with rounds, sample 5 with the line with x, sample 5 added with mannitol (5m) with the dark line with diamonds. From top to bottom, the lines of samples 3m, 4m, 3, 5m, 5, 4 are visible.
Figure 12:
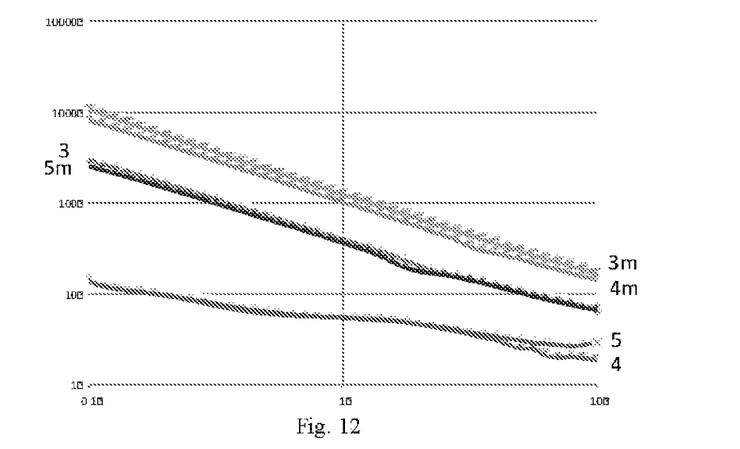
FIG. 12 shows the rheological properties of the samples mentioned in table 9 below, prepared according to example 6, where the X axis shows the frequency in Hz and the Y axis shows the complex viscosity in Pa*s. Sample 3 is represented with the line with vertical bars, sample 3 added with mannitol (3m) with the line with squares, sample 4 with the clear line with diamonds, sample 4 added with mannitol (4m) with the clear line with rounds, sample 5 with the line with x, sample 5 added with mannitol (5m) with the dark line with diamonds. From top to bottom, the lines of samples 3m, 4m, 3, 5m, 5, 4 are visible.

The gels were prepared as in example 5. Mannitol was added to the samples at a final concentration of 220 mM mannitol. These samples were obtained by dissolving mannitol in the solution of pectin. The gels were then subjected to beta radiation at 25 KGy and subsequently analyzed by the rheological tests. The storage module and the complex viscosity of each gel were quantified according to rheological measurements carried out as described in example 4. These measurements are shown in FIGS. 11 and 12.

The invention claimed is:
1. A composite biocompatible gel material comprising an aqueous solution of pectin and a solution/suspension of calcium phosphate mixed together, wherein in said gel material the concentration of pectin is greater than the concentration of calcium phosphate, and wherein said gel material further comprises said pectin cross-linked with at least one portion of calcium phosphate and at least one second portion of calcium phosphate trapped to form an inorganic phase of calcium phosphate.

2. The composite biocompatible gel material according to claim 1, wherein said calcium phosphate is present in the aqueous solution at a concentration of between 0.1 and 10% weight/volume and said pectin is present in the aqueous solution at a concentration between 0.2 and 10% weight/volume.

3. The composite biocompatible gel material according to claim 1, wherein said pectin has a percentage of esterification of between 5% and 50%.

4. The composite biocompatible gel material according to claim 1, wherein said percentage of esterification is at least one of 42% or 40%.

5. The composite biocompatible gel material according to claim 1, wherein said pectin has a molecular weight between 40 and 350 kDa.

6. The composite biocompatible gel material according to claim 1, wherein said pectin has a molecular weight between 15 and 1000 kDa.

7. The composite biocompatible gel material according to claim 1, wherein said calcium phosphate is present in solution/suspension at a concentration of between 0.25% and 5% weight/volume.

8. The composite biocompatible gel material according to claim 1, wherein said solution/suspension includes calcium phosphate at a concentration of between 0.25% and 3%.

9. The composite biocompatible gel material according to claim 1, wherein said calcium phosphate comprises at least one of the following types: calcium phosphate $Ca_3(PO_4)_2$, calcium dihydrogen phosphate $Ca(H_2PO_4)_2$, calcium hydrogen phosphate $CaHPO_4$, tricalcium phosphate β or α $Ca_3(PO_4)_2$, tetracalcium phosphate $Ca_4(PO_4)_2$, hydroxyapatite $Ca_{10}(PO_4)_6(OH)_2$, acid calcium phosphate, calcium glycerophosphate, calcium lactophosphate, tribasic calcium phosphate, calcium o-phosphate and calcium pyrophosphate.

10. The composite biocompatible gel material according to claim 1, wherein said composite material includes equal portions of the solution of pectin and of said solution/suspension of calcium phosphate mixed together.

11. The composite biocompatible gel material according to claim 1, wherein said composite material includes from 0.2 parts to 2 parts of said solution of pectin, and one part of said solution/suspension of calcium phosphate.

12. The composite biocompatible gel material according to claim 1, comprising mannitol.

13. The composite biocompatible gel material according to claim 12, wherein said mannitol has a final concentration of between 50 and 500 mM.

14. The composite biocompatible gel material according to claim 12, wherein said mannitol has a final concentration of 220 mM.

15. The composite biocompatible gel material according to claim 1, wherein said material is loaded with active substances against the reduction of the infection, including metal ions known for antibacterial effectiveness and/or topical antimicrobial drugs and/or wherein said calcium phosphate is pre-loaded with said metal ions known for their antibacterial effectiveness, including silver or zinc and/or wherein said pectin is suitable for conveying drugs and/or specific medicinal substances.

16. The composite biocompatible gel material obtainable according to claim 1, for use in medical applications as a medicine for aesthetic applications and/or treatment of skin lesions and/or for the treatment of cartilage defects and/or as a bone substitute.

* * * * *